(12) United States Patent
De Martino et al.

(10) Patent No.: US 10,094,766 B2
(45) Date of Patent: Oct. 9, 2018

(54) DEVICE AND METHOD FOR REMOTE POLARIMETRIC CHARACTERIZATION

(71) Applicants: Centre National de la Recherche Scientifique—CNRS, Paris (FR); Ecole Polytechnique, Palaiseau (FR)

(72) Inventors: Antonello De Martino; Dominique Pagnoux, Limoges (FR); Jérémy Vizet, Limoges (FR); Sandeep Manhas, Limoges (FR); Jean-Charles Vanel, Paris (FR); Stanislas Deby, Boulogne Billancourt (FR)

(73) Assignees: CENTRE NATIONAL DE LA RECHERCHE SCIENTIFIQUE-CNRS, Paris (FR); Ecole Polytechnique, Palaiseau (FR)

( * ) Notice: Subject to any disclaimer, the term of this patent is extended or adjusted under 35 U.S.C. 154(b) by 0 days.

(21) Appl. No.: 15/126,798

(22) PCT Filed: Feb. 18, 2015

(86) PCT No.: PCT/EP2015/053437
§ 371 (c)(1),
(2) Date: Sep. 16, 2016

(87) PCT Pub. No.: WO2015/139907
PCT Pub. Date: Sep. 24, 2015

(65) Prior Publication Data
US 2017/0102319 A1  Apr. 13, 2017

(30) Foreign Application Priority Data
Mar. 18, 2014 (FR) ...................... 14 52244

(51) Int. Cl.
G01J 4/00 (2006.01)
G01N 21/21 (2006.01)
A61B 1/07 (2006.01)

(52) U.S. Cl.
CPC ............... *G01N 21/21* (2013.01); *A61B 1/07* (2013.01); *G01N 2201/0636* (2013.01);
(Continued)

(58) Field of Classification Search
CPC ...... G01N 21/21; G01N 21/211; G01N 21/23; G01J 4/04; G01J 4/00
(Continued)

(56) References Cited

U.S. PATENT DOCUMENTS

2009/0119808 A1* 5/2009 Giakos .................. G01Q 60/22
850/31

OTHER PUBLICATIONS

Ji Qi et al "Narrow Band 3X3 Mueller Polarimetric Endoscopy" vol. 4, No. 11, 2013, ISSN: XP055152270.*
(Continued)

*Primary Examiner* — Md M Rahman
(74) *Attorney, Agent, or Firm* — Osha Liang LLP

(57) ABSTRACT

According to one aspect, the invention relates to a device (100) for remote polarimetric characterization of a sample (S). It comprises a source (10) for emitting at least one incident light wave at at least one first wavelength ($\lambda_E$); a monomode optical fiber (30) in which the incident light wave is intended to propagate; a polarization state generator (PSG) arranged on the proximal side of the optical fiber; a reflector (40) intended to be arranged on the distal side of the optical fiber; a polarization state analyzer (PSA) arranged on the proximal side of the optical fiber and allowing, for each probe state of the incident wave generated by the polarization state generator, the polarization of the light wave obtained after propagation of the incident wave in the optical fiber (30), reflection from the distal side of the optical fiber
(Continued)

and reverse propagation in the optical fiber (30), to be analyzed. Processing means (70) make it possible to determine, from a first polarimetric characterization of the optical fiber, a Mueller matrix ($M_F$) associated with the optical fiber, and, from a second polarimetric characterization of the assembly comprising the optical fiber and the sample, a Mueller matrix ($M_T$) associated with said assembly. The Mueller matrix ($M_o$) associated with the sample is determined from the Mueller matrices associated with the optical fiber and the assembly comprising the optical fiber and the sample, respectively.

14 Claims, 11 Drawing Sheets

(52) U.S. Cl.
 CPC . *G01N 2201/0683* (2013.01); *G01N 2201/08* (2013.01); *G01N 2201/12* (2013.01)
(58) Field of Classification Search
 USPC ........................................................ 356/364
 See application file for complete search history.

(56) References Cited

OTHER PUBLICATIONS

International Search Report issued in PCT/EP2015/053437, dated Jun. 5, 2015 (1 page).
Written Opinion of the International Searching Authority issued in PCT/EP2015/053437, dated Jun. 5, 2015 (7 pages).

\* cited by examiner

| H | V | P | M | L | R | A |
|---|---|---|---|---|---|---|
| $\begin{bmatrix} 1 \\ 1 \\ 0 \\ 0 \end{bmatrix}$ | $\begin{bmatrix} 1 \\ -1 \\ 0 \\ 0 \end{bmatrix}$ | $\begin{bmatrix} 1 \\ 0 \\ 1 \\ 0 \end{bmatrix}$ | $\begin{bmatrix} 1 \\ 0 \\ -1 \\ 0 \end{bmatrix}$ | $\begin{bmatrix} 1 \\ 0 \\ 0 \\ 1 \end{bmatrix}$ | $\begin{bmatrix} 1 \\ 0 \\ 0 \\ -1 \end{bmatrix}$ | $\begin{bmatrix} 1 \\ \cos 2\theta \cos 2\varepsilon \\ \sin 2\theta \cos 2\varepsilon \\ \sin 2\varepsilon \end{bmatrix}$ |

PRIOR ART

FIG.1C

DEVICE AND METHOD FOR REMOTE POLARIMETRIC CHARACTERIZATION

STATE OF THE ART

Technical Field

The present invention relates to a method and a device for remote polarimetric characterization through an optical fiber and applies notably to endoscopy for the in vivo polarimetric characterization of biological tissues.

State of the Art

It is known practice to describe the polarization state of an electromagnetic wave (of which notably the visible light) by a set of four values called Stokes parameters, often denoted in the form of a vector, the Stokes vector $\vec{S}$:

$$\vec{S} = \begin{pmatrix} I_x + I_y \\ I_x - I_y \\ I_{45°} - I_{-45°} \\ I_G - I_D \end{pmatrix} = \begin{pmatrix} I \\ Q \\ U \\ V \end{pmatrix} = \begin{pmatrix} S_0 \\ S_1 \\ S_2 \\ S_3 \end{pmatrix} \quad (1)$$

The Stokes vector comprises four components generally denoted I, Q, U, V and which respectively describe the total intensity I of the beam ($I=I_x+I_y$), the differences between the horizontal and vertical components of the electrical field ($I_x-I_y$), at ±45° ($I_{45°}-I_{-45°}$) and left and right circular ($I_G-I_D$). They make it possible to completely describe the non-polarized, partially polarized and totally polarized light.

The Poincaré sphere is a graphic representation of the polarization of the light, an example of which is illustrated in FIG. 1A. A generic Stokes vector is represented by its reduced coordinates $q=Q/I$, $u=U/I$ and $v=V/I$ which define the polarization state independently of the overall intensity. The totally polarized states are located on the surface of the sphere, of unity radius (for example the point referenced A in FIG. 1A). The partially polarized states, of which the degree of polarization p is defined by:

$$p = q^2 + u^2 + v^2 \quad (2)$$

are situated inside the sphere, at a distance p<1 from the center (for example the point referenced B in FIG. 1A). The polar coordinates ε and θ respectively define the ellipticity and the azimuth of the major axis of a generally elliptical polarization as represented in FIG. 1B.

FIG. 1C thus shows examples of Stokes vectors of polarized waves, of given polarizations, respectively Stokes vectors corresponding to a horizontal linear polarization (H), a vertical linear polarization (V), linear polarizations oriented at ±45° (P and M), right (R) and left (L) circular polarizations and an elliptical polarization (A), each of the corresponding polarization states being, moreover, represented by a point on the Poincaré sphere represented in FIG. 1A.

The Mueller matrix of a sample is a set of sixteen data which completely determine the polarimetric response of this sample and constitute a means for structural characterization thereof. The technique making it possible to measure this matrix, called "Mueller polarimetry", consists in illuminating the sample with at least four different polarization states and in analyzing the polarization states returned, as illustrated in FIG. 2. More specifically, a source of light emission, for example a laser or a laser diode, makes it possible to send a light beam into a device called "polarization state generator" or PSG to generate four given and known light polarization states ("probe polarization states"), each defined by a Stokes vector as described previously. The PSG consists, for example, of a succession of polarizers and of retardation plates which characteristics can be changed, for example by electrical control. These plates can, for example, consist of liquid crystal plates oriented by the application of an electrical control voltage. For each of the four polarization states outgoing from the PSG, the polarization state of the light returned by the sample is analyzed using a "polarization state analyzer" or PSA. The PSA makes it possible to measure the intensity of the light wave returned through four polarization filters which can be identical to those which made it possible to generate the probe polarization states. For example, the PSA can be "the mirror image" of the PSG, with the same components, but passed through in the reverse order. The PSA can also be different from the PSG, but in all cases, it must implement at least four different polarization filters to completely determine the Stokes vector of the light emerging from the sample. Finally, at least sixteen intensity measurements are thus performed making it possible to construct the Mueller matrix of the sample.

Different studies have shown how the analysis of the coefficients of the Mueller matrix makes it possible to obtain the polarimetric information concerning the characterized sample (linear and circular birefringence, linear and circular diattenuation (or dichroism), depolarization rate). For example, Lu and Chipman (S. Lu et al. "Interpretation of Mueller matrices based on polar decomposition", J. Opt. Soc. Am. A 13, 1106-1113 (1996)) have demonstrated that it is possible to decompose a non-degenerated Mueller matrix into a product of matrices, each being characteristic of a specific optical effect, namely the depolarization (reduction of the degree of polarization as defined in the equation (2) above upon the interaction with the sample), the linear or circular delay (or phase delay introduced between two orthogonal linear or opposite circular polarization states) and the linear or circular diattenuation (or transmission difference introduced between two orthogonal linear or opposing circular linear polarization states).

The polarimetric information then makes it possible to determine, on biological samples, information on the physical-chemical structure of the materials analyzed. For example, the depolarization, which represents the greatest effect in the thick tissues (except for those of the eye), is due primarily to the multiple scattering of the light on objects such as the fibers or collagen nodules, the intracellular organelles, the nuclei, etc. The linear delay is observed on thin tissues (histological plates) or thick tissues in the presence of fibrillar proteins, such as collagen I, if these fibers exhibit a preferential orientation. The diattenuation is generally negligible, except in the case of tissues observed under glancing incidence, where the crossing of the interface can create a significant diattenuation, the polarization in the plane of incidence being better transmitted than that at right angles to this plane.

Thus, ex-vivo studies of colon samples (see A. Pierangelo et al. Opt. Express 19, 1582-1593 (2011)) have shown that these samples behave as pure depolarizers, and that the depolarization supplies useful contrasts for the detection of tumors at an early stage (they depolarize less than the surrounding healthy tissue), for the assessment of the degree of penetration of more advanced tumors or even for the detection of residual tumors after radio chemotherapy (A. Pierangelo et al. J. Biomed. Opt. 18, 046014 (2013)). In the case of the analysis of the uterine cervix tissues (A. Pierangelo et al; Opt. Express 21, 14120-30 (2013)), both depolarization and delay are observed, the latter being present only in the healthy zones, of which it therefore constitutes a powerful marker. The depolarization, for its part, makes it possible to distinguish the healthy zones from those exhibiting precancerous lesions (dysplasias). The published patent application WO 2007003840 shows how the Mueller polarimetry can be added to complement a colposcope, that is to say a binocular microscope with long working distance intended for the in vivo detailed examination of the uterine cervix.

For the analysis of biological objects in vivo, or more generally any object difficult to access, there is an obvious interest in performing a remote polarimetry characterization, making it possible to distance the object to be analyzed from the source/PSG assemblies on the one hand and PSA/detection/analysis assemblies on the other hand. Such a remote characterization can be done by means of a light guide like an optical fiber for example. In this case, the polarization states sent by the PSG into the optical fiber towards the object are known, and, with the PSA, it is possible to analyze the polarization states of the light originating from the object, after they have passed through the optical fiber in return. However, this optical fiber induces perturbations of the polarization states of the light which passes through it, both on the forward path (path from the source to the object of interest) and on the backward path (path from the object to the detection and analysis system). These unpredictable and uncontrollable perturbations are strongly dependent on the conditioning of the optical fiber (bends, twists, etc.) and on the environment (temperature, etc.). They prevent from knowing the polarization states actually incident on the object, and from having access to the polarization states which are returned by this object in the optical fiber and which should be analyzed. In these conditions, the characterization of the object by Mueller polarimetry is no longer possible.

Solutions have recently been proposed for attempting to overcome the perturbations induced by the optical fiber, or more generally by the waveguide used to distance the object to be analyzed, in order to access polarimetric information of a sample.

In the published patent application FR 2941047, a linearly polarized wave is sent through a device capable of generating a large number of polarization states well distributed over the Poincaré sphere, these polarization states being sent through a waveguide, then reflected on the object, and the polarization of the reflected wave being analyzed after having passed through the waveguide in return. A Faraday rotator is positioned on the distal side, that is to say on the side of the end of the waveguide at which the object to be analyzed is located, the Faraday rotator allowing a rotation of 45° of the polarization. This Faraday rotator has the effect of compensating, for each polarization state sent to the object, the delay introduced by the fiber. For each of these probe polarization states, the fraction F of the intensity detected in return, carried by the polarization parallel to the linear polarization sent, is measured. From all the measured fractions F, dependent on the probe polarization states, the minimum value $F_{min}$ and the maximum value $F_{max}$ are determined from which the depolarization rate and the phase delay introduced by the object are deduced. However, this technique does not allow access to the diattenuation or to the circular dichroism of the sample.

More recently, a device with polarimetric measurement through a single-mode fiber has been described (see for example the patent application FR 2977033 of Alouni et al.) which makes it possible to detect whether the orthogonality of two incident polarizations on the object of analysis has been broken, which may be due to the depolarization or the diattenuation due to the object, but without being able to make the distinction between these two effects. Furthermore, the delay possibly introduced by the object cannot be measured by this method.

The paper by Wood et al. (T. C. Wood et al. "Polarization response measurement and simulation of rigid endoscopes", Biomedical Optics express 463, Vol. 1, No 2 (2010)) highlights and characterizes, in commercial rigid endoscopes (also called laparoscopes), birefringence effects in particular, which are attributed to an input window of sapphire. The article suggests replacing the sapphire with a material that is not birefringent and that is compatible with the constraints linked to the sterilization for limiting these birefringence effects and allows remote comprehensive polarimetric characterizations on samples in vivo. Residual birefringence effects can nevertheless remain, which can prove to be a nuisance, above all if they vary in time or with the position of the instrument.

Qi et al. also describe a laparoscope equipped with a linear polarizer with the distal end and a wheel with linear polarizers with different orientations on the proximal side (Qi et al., "Narrow band 3×3 polarimetric endoscopy", Biomedical Optics Express, vol 4 no 11, (2013)). This apparatus allows the acquisition of partial Mueller matrices, limited to the first three lines and first three columns, through the rotation of the instrument about its axis to vary the orientation of the polarizer on detection. This approach presents two limitations: on the one hand, there is no access to the circular delays and diattenuation, and, on the other hand, the rotation of the instrument about its axis is really impractical in real examination conditions, because, in particular, of the need to perform this rotation about the axis of the endoscope with excellent precision, to avoid having the image move in the field between two acquisitions. Even if this condition is fulfilled, there is a fear of "nonrigid" deformations of the organs examined in vivo occurring during the rotation, which can disqualify the method in many situations.

The present invention proposes a method and a system for remote characterization which make it possible to access, by means of a flexible optical fiber, a characterization of the complete Mueller matrix of a sample. It is thus possible to have access simultaneously to all the polarimetric information of the sample, including the linear and circular diattenuations and delays. This complete characterization of the Mueller matrix offers numerous advantages for the analysis of biological samples in particular. Indeed, even if in most cases the tissues exhibit essentially linear intrinsic effects, it is possible to simultaneously observe, under glancing incidence (which can be commonplace in endoscopy), a significant diattenuation on passing through the surface of the tissue, which can give rise to a circular diattenuation if, moreover, the tissue exhibits linear birefringence.

SUMMARY

According to a first aspect, the present description relates to a device for remote polarimetric characterization of a sample comprising:
- a source of emission of at least one incident light wave at at least one first wavelength;
- a single-mode optical fiber in which the incident light wave is intended to be propagated;
- a polarization state generator arranged on the proximal side of the optical fiber and allowing the generation of a given number of polarization states of the incident light wave, called probe states;

a reflector intended to be arranged on the distal side of the optical fiber;

a polarization state analyzer arranged on the proximal side of the optical fiber and allowing, for each probe state of the incident wave, the analysis of the polarization of the light wave obtained after propagation of the incident wave in the optical fiber, reflection on the distal side of the optical fiber and reverse propagation in the optical fiber;

processing means making it possible to determine:
a Mueller matrix associated with the optical fiber at the first wavelength from a first polarimetric characterization of the optical fiber, obtained by the analysis of each probe state, of the polarization of at least one wave reflected on the distal side of the optical fiber by means of the reflector;
a Mueller matrix associated with said assembly at the first wavelength, from a second polarimetric characterization of the assembly comprising the optical fiber and the sample, obtained by the analysis for each probe state of the polarization, of a wave returned by the sample from the distal side of the fiber and propagated in the reverse direction in the optical fiber;
the Mueller matrix associated with the sample at the first wavelength from the Mueller matrices associated respectively with the optical fiber and with the assembly comprising the optical fiber and the sample.

The original arrangement of the polarimetric characterization device makes it possible to have access to all the polarimetric information of a sample by virtue of a complete determination of the Mueller matrix of that sample.

According to one or more exemplary embodiments, the source of emission allows the emission of a wave at the first wavelength and the emission of a wave at a second wavelength distinct from the first wavelength.

According to one or more exemplary embodiments, the reflector is advantageously a spectral reflector allowing the reflection of a wave being propagated in the optical fiber at the second wavelength for the polarimetric characterization of the optical fiber at the second wavelength and the passage of the wave at the first wavelength for the polarimetric characterization of the assembly comprising the optical fiber and the sample at the first wavelength. The processing means make it possible to determine:
from the polarimetric characterization of the optical fiber at the second wavelength, a Mueller matrix associated with the optical fiber at the second wavelength;
from the Mueller matrix associated with the optical fiber at the second wavelength, a Mueller matrix associated with the optical fiber at the first wavelength.

This first variant based on a chromatic separation of the light waves allows for a simultaneous determination of the Mueller matrices of the optical fiber on the one hand and of the assembly comprising the optical fiber and the sample on the other hand. Moreover, it does not require active optical elements on the distal side of the optical fiber.

According to one or more exemplary embodiments, the two wavelengths are distinct but close; typically, the difference between the two wavelengths does not exceed 100 nm.

According to one or more exemplary embodiments, when the phase delay generated by the optical fiber is greater than $2\pi$, the characterization of the optical fiber can be done by means of two distinct wavelengths.

Thus, according to this example, the source of emission also allows the emission of a wave at a third wavelength distinct from the first and second wavelengths. The spectral reflector allows the reflection of waves being propagated in the optical fiber at the second and third wavelengths for the polarimetric characterization of the optical fiber at the second and third wavelengths. Moreover, the processing means make it possible to determine:
from a polarimetric characterization of the optical fiber at the second wavelength and from a polarimetric characterization of the optical fiber at the third wavelength, respectively a Mueller matrix associated with the optical fiber at the second wavelength and a Mueller matrix associated with the optical fiber at the third wavelength;
from the Mueller matrices associated with the optical fiber at the second and third wavelengths, the Mueller matrix associated with the optical fiber at the first wavelength.

Here too, the wavelengths are distinct but remain close, the difference between the wavelengths advantageously remaining less than 100 nm.

According to one or more exemplary embodiments, the reflector is a reflector that can be switched between a reflecting position and a passing position. Such a reflector allows, in the reflecting position, the reflection of a wave being propagated in the optical fiber at the first wavelength for the polarimetric characterization of the optical fiber and, in the passing position, the reflection of the wave by the sample for the polarimetric characterization of the assembly comprising the optical fiber and the sample.

This second variant offers the advantage of being able to proceed with the characterization of the optical fiber directly at the first wavelength, that is to say at the wavelength used to characterize the assembly comprising the optical fiber and the sample. This notably allows for a greater flexibility in the choice of the single-mode optical fiber used.

According to one or more exemplary embodiments, and whatever the variant implemented, the single-mode optical fiber is a polarization-maintaining optical fiber, which eliminates any chiral effect.

According to one or more exemplary embodiments, the single-mode optical fiber comprises a first section of a polarization-maintaining single-mode optical fiber and a second section of the same polarization-maintaining single-mode optical fiber, the sections being of the same length and connected together in such a way that the fast axis of the first section is aligned with the slow axis of the second section, and vice versa.

This fiber example notably makes it possible to reduce the phase delay introduced by the fiber while eliminating any chiral effect, thus facilitating the characterization thereof.

According to one or more exemplary embodiments, the device according to the first aspect further comprises, on the distal side of the optical fiber, means for focusing a wave at the first wavelength for the characterization of a spot zone of the sample.

According to one or more exemplary embodiments, the device according to the first aspect further comprises, on the distal side of the optical fiber, scanning means for the polarimetric characterization of a set of spot zones of the sample.

According to a second aspect, the present description relates to one or more method(s) for remote polarimetric characterization of a sample implemented by the device(s) according to the first aspect.

Thus, the invention relates to a method for remote polarimetric characterization of a sample comprising:
the emission of an incident light wave at at least one first wavelength intended to be propagated in a single-mode optical fiber;

the polarimetric characterization of the optical fiber at the first wavelength, comprising:

the generation of a given number of polarization states of the incident light wave, called probe states, by means of a polarization state generator arranged on the proximal side of the optical fiber;

the analysis, for each probe state of the incident wave, of the polarization of the light wave obtained after propagation of the incident wave in the optical fiber, reflection by means of a reflector arranged on the distal side of the optical fiber and back propagation in the optical fiber;

the determination of a Mueller matrix associated with the optical fiber at the first wavelength;

the polarimetric characterization of the assembly comprising the optical fiber and the sample at the first wavelength, comprising:

by means of said polarization state generator and polarization state analyzer, the analysis, for each probe state of the polarization, of a wave returned from the distal side of the fiber by the sample and propagated in the backward direction in the optical fiber;

the determination of a Mueller matrix associated with said assembly at the first wavelength;

the determination of the Mueller matrix associated with the sample from the Mueller matrices associated respectively with the optical fiber and with the assembly comprising the optical fiber and the sample.

According to one or more exemplary embodiments, the method further comprises the emission of a light wave at a second wavelength distinct from the first wavelength. According to this variant, the reflector is a spectral reflector allowing the reflection of a wave being propagated in the optical fiber at the second wavelength for the polarimetric characterization of the optical fiber at the second wavelength and the passage of the wave at the first wavelength for the polarimetric characterization of the assembly comprising the optical fiber and the sample at the first wavelength. Moreover, the determination of the Mueller matrix associated with the optical fiber at the first wavelength comprises:

from the polarimetric characterization of the optical fiber at the second wavelength, a Mueller matrix associated with the optical fiber at the second wavelength;

from the Mueller matrix associated with the optical fiber at the second wavelength, a Mueller matrix associated with the optical fiber at the first wavelength.

According to one or more exemplary embodiments, the method comprises the emission of a wave at a third wavelength distinct from the first and second wavelengths, and the spectral reflector allows the reflection of waves being propagated in the optical fiber at the second and third wavelengths for the polarimetric characterization of the optical fiber at the second and third wavelengths; the determination of the Mueller matrix associated with the optical fiber at the first wavelength comprises:

from a polarimetric characterization of the optical fiber at the second wavelength and from a polarimetric characterization of the optical fiber at the third wavelength, respectively a Mueller matrix associated with the optical fiber at the second wavelength and a Mueller matrix associated with the optical fiber at the third wavelength;

from the Mueller matrices associated with the optical fiber at the second wavelength and third wavelength, the Mueller matrix associated with the optical fiber at the first wavelength.

According to one or more exemplary embodiments, the reflector is a reflector that can be switched between a reflecting position and a passing position, allowing, in the reflecting position, the reflection of a wave being propagated in the optical fiber at the first wavelength for the polarimetric characterization of the optical fiber and, in the passing position, the reflection of the wave by the sample for the polarimetric characterization of the assembly comprising the optical fiber and the sample.

According to one or more exemplary embodiments, the method according to one of the variants described previously further comprises, on the distal side of the optical fiber, the focusing of a light wave at the first wavelength at the focusing means for the characterization of a spot zone of the sample.

The method can also comprise, on the distal side of the optical fiber, the scanning, by scanning means, of the focused light wave for the polarimetric characterization of a set of spot zones of the sample.

BRIEF DESCRIPTION OF THE DRAWINGS

Other advantages and features will become apparent on reading the description, illustrated by the following figures:

FIG. 1C, a table showing the components of Stokes vectors of different polarization states (already described);

DETAILED DESCRIPTION

Figure 1A:
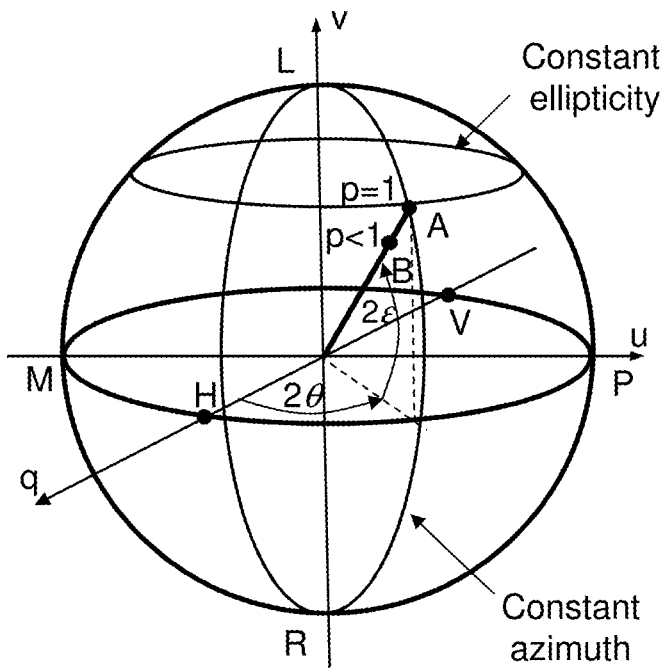
FIGS. 1A and 1B, a representation of the Poincaré sphere and of an elliptical polarization state (already described)
Figure 1B:
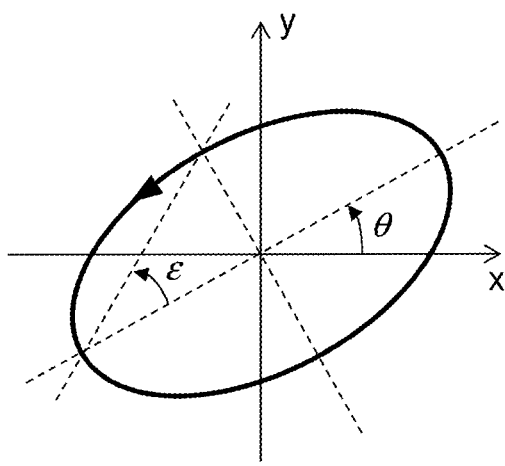
Figure 2:
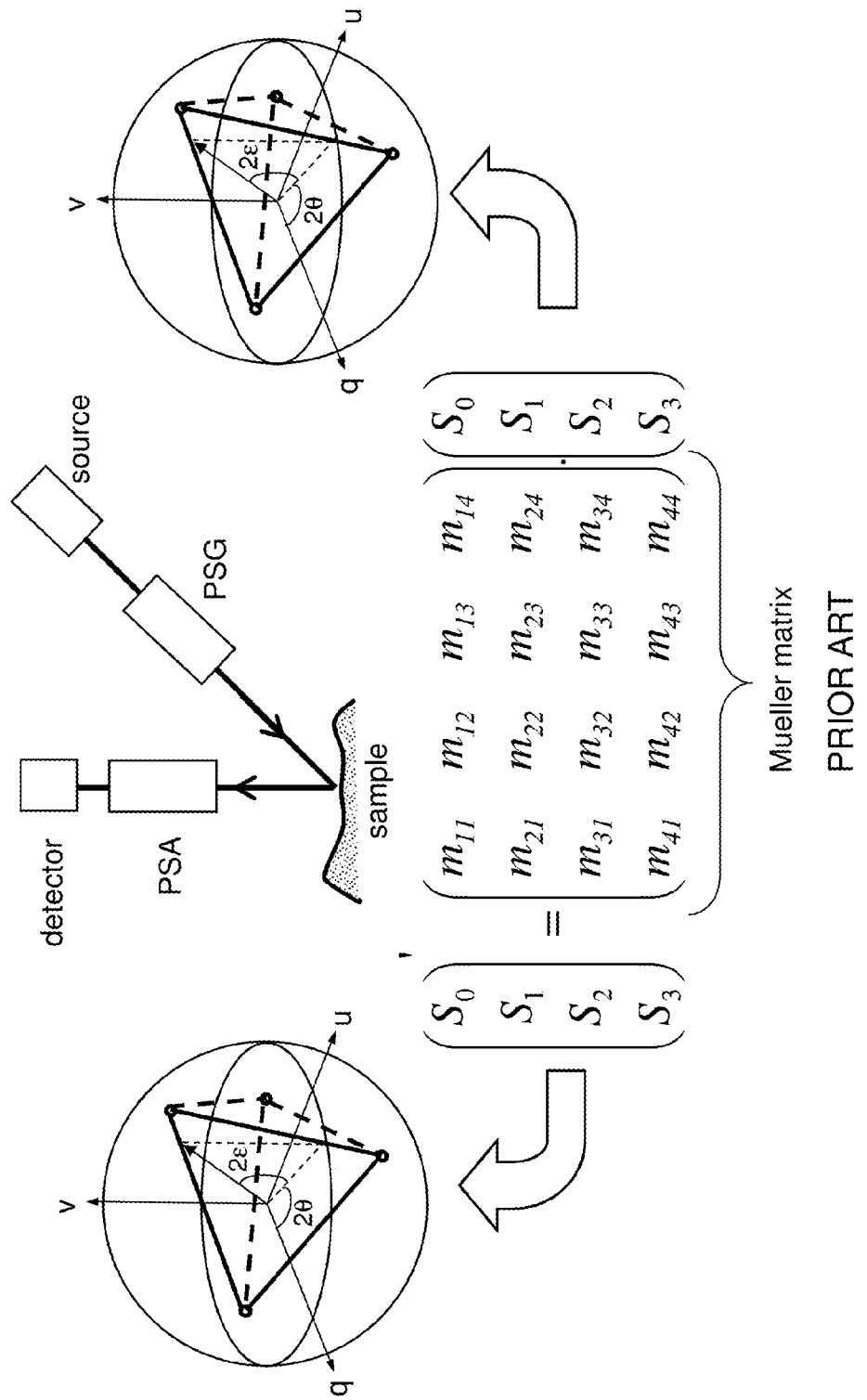
FIG. 2, a diagram illustrating an experimental setup for a characterization by Mueller polarimetry according to the prior art (already described)
Figure 3:
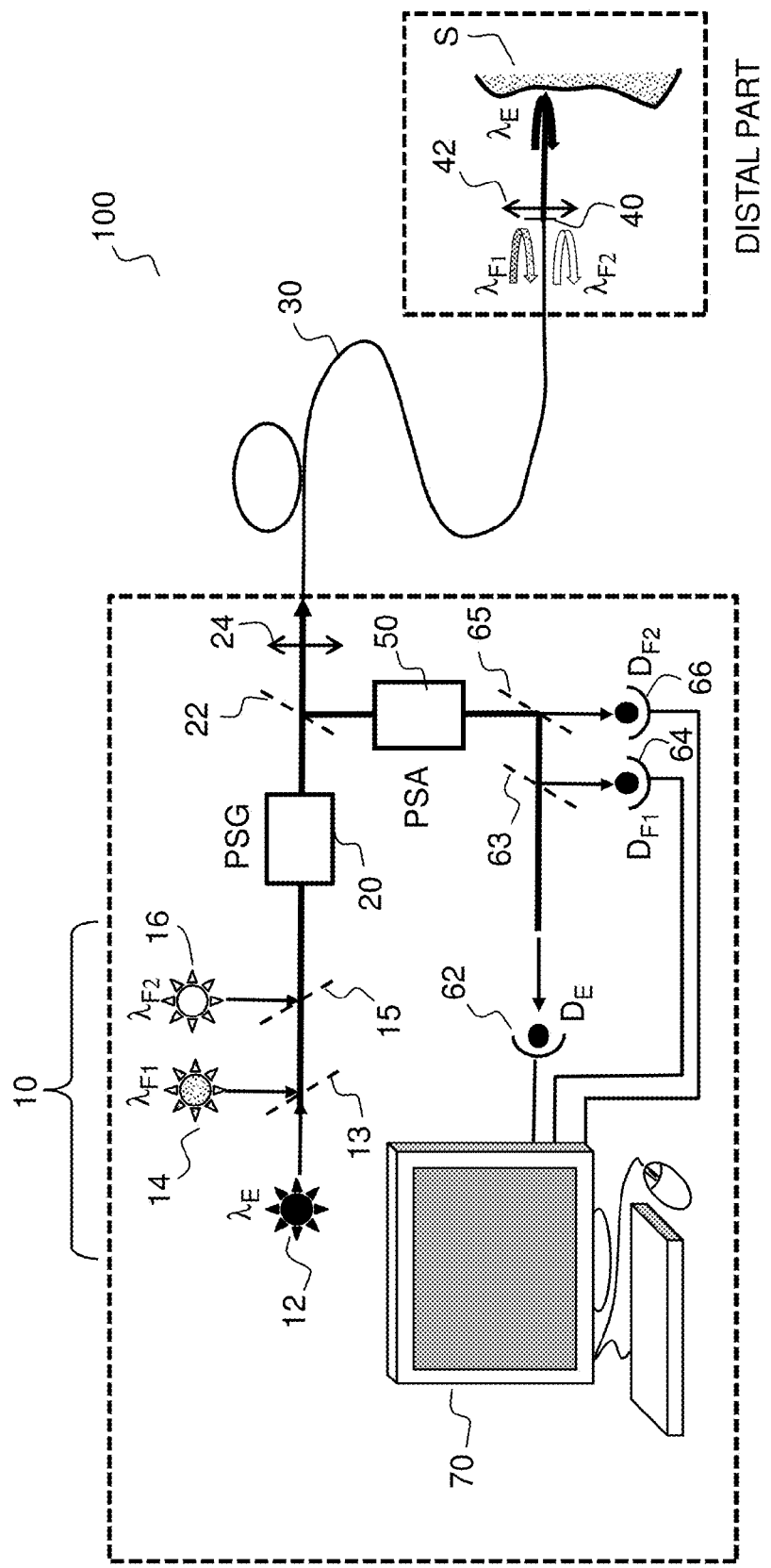
FIG. 3, a diagram illustrating a polarimetric characterization device according to the present description, according to a first example.

FIG. 3 represents a polarimetric characterization device 100 according to a first example, for the implementation of a polarimetric characterization method according to a first aspect of the present description.

The polarimetric characterization device 100 generally comprises a source of emission 10 of at least one light wave at at least one first wavelength $\lambda_E$ and a single-mode optical fiber 30 in which the light wave is intended to be propagated for a remote characterization of a sample S. A single-mode optical fiber notably offers the advantage over a multimode fiber of not depolarizing the incident light even though it may be caused, according to its nature and the experimental conditions, to modify the polarization. The sample to be analyzed or "an object of analysis" S is situated, relative to the source of emission 10, at the other end of the optical fiber 30.

Hereinafter in the description, all the part of the device situated on the side of the optical fiber where the source of emission is located will be called proximal part and all the part of the device situated at the other end of the optical fiber, that is to say where the sample is located, will be called distal part.

The device 100 further comprises a polarization state generator PSG arranged on the proximal side of the optical fiber and allowing the generation of a given number of polarization states of the light wave (probe polarization states) and a polarization state analyzer PSA arranged on the proximal side of the optical fiber and allowing the analysis of the polarization states of the light wave after reflection on the distal side of the optical fiber and reverse propagation in the optical fiber.

In the example of FIG. 3, the source 10 allows the emission of a wave at a first wavelength $\lambda_E$ and the emission of at least one wave at a second wavelength $\lambda_{F1}$ distinct from the first wavelength $\lambda_E$. According to a variant which will be described in detail hereinbelow, the source 10 allows the emission of two waves respectively at the wavelengths $\lambda_{F1}$ and $\lambda_{F2}$, distinct from one another and distinct from $\lambda_E$. The source 10 comprises, for example, a set of monochromatic sources, for example laser diodes, respectively denoted 12, 14, 16 in FIG. 3, each emitting at one of the distinct wavelengths. Alternatively, the source 10 can consist of a single source emitting at all the wavelengths, for example a source of "supercontinuum source" type generated by spectral broadening of a laser beam within an optical fiber.

Advantageously, the sources of emission are continuous sources. Alternatively, they can be pulsed sources of peak power that are low enough not to generate nonlinear optical effects in the optical fiber. Another option consists in using a continuous source modulated by a chopper and implementing a synchronous detection on all the detectors, in order to improve, if necessary, the signal-to-noise ratio relative to a continuous source. In this case, the modulation is advantageously performed at a frequency much higher than the switching frequency of the liquid crystals of the PSG and PSA, which is at most of the order of a kHz, which does not pose any problem in principle, the synchronous detection being typically implemented up to frequencies of 100 kHz with market-standard systems.

The polarimetric characterization device further comprises, in the example described in FIG. 3, a wavelength-selective reflector 40, arranged on the distal side of the optical fiber, and focusing means 42. The reflector 40 makes it possible to reflect the waves at the wavelength $\lambda_{F1}$, or at the wavelengths $\lambda_{F1}$ and $\lambda_{F2}$, while allowing the wavelengths at the wavelength $\lambda_E$ to pass. The reflector 40 is for example a spectral filter placed at the output of the optical fiber 30; this filter can, for example, be a high-pass filter cutting off between $\lambda_{F2}$ and $\lambda_E$, if $\lambda_{F1}<\lambda_{F2}<\lambda_E$ is chosen. This filter can also, for example, be a bandpass filter around $\lambda_E$ if $\lambda_{F1}<\lambda_E<\lambda_{F2}$ is chosen or a low-pass filter if $\lambda_E<\lambda_{F1}<\lambda_{F2}$ is chosen.

The polarimetric characterization device 100 moreover comprises a separating plate 22 and wavelength separator elements 65, 63, for example spectral filters, arranged after the polarization state analyzer PSA, and making it possible to split, according to the wavelength, the waves retroreflected or backscattered on the distal side of the fiber and back guided in the fiber. The duly split light waves are sent to photodetectors, respectively denoted $D_E$, $D_{F1}$, $D_{F2}$ in FIG. 3, for example photodiodes, sensitive respectively to the wavelengths $\lambda_E$, $\lambda_{F1}$ and $\lambda_{F2}$.

The polarimetric characterization device 100 also comprises processing means 70 making it possible, from the electronic signals emitted by the photodetectors, to determine the Mueller matrix of the sample S, as is described hereinbelow. The processing means 70 notably ensure the control and the synchronization of the PSG and PSA, the collection and the processing of the signals emitted by the photodetectors, the construction of the Mueller matrices.

The general principle of the polarimetric characterization method according to the first variant implemented for example by means of a device as described in FIG. 3 is based on simultaneous measurements made at different but close wavelengths, typically separated by less than 100 nm, to characterize the optical fiber on the one hand and the fiber-object assembly on the other hand. More specifically, one or two wavelengths can be used to characterize the fiber ($\lambda_{F1}$ and $\lambda_{F2}$), and one is sufficient for the fiber-object of interest assembly ($\lambda_E$).

Thus, light waves, for example monochromatic or quasi-monochromatic waves (typically of spectral widths less than 40 nm) are sent into the single-mode optical fiber 30 by means of an injection lens 24. After passing through the wavelength-selective reflector 40, the beam at the wavelength $\lambda_E$ is focused on the object by the focusing means 42, for example a lens or any other optical element capable of producing the focusing function. A part of the light returned by this object, still at $\lambda_E$, passes back through the focusing optical element 42 and the spectral filter 40 to be reinjected into the optical fiber 30. The beam(s) at the wavelengths different from $\lambda_E$, in this example the wavelengths $\lambda_{F1}$ and $\lambda_{F2}$, are, for their part, reflected by the spectral filter 40 and reinjected into the optical fiber 30 without being impacted by the sample S. In return, all of the beams at $\lambda_{F1}$, $\lambda_{F2}$ and $\lambda_E$ are deflected toward the PSA, then split at the output of the PSA by means of the separator elements 65, 63 to the detectors 62, 64, 66. In the case of the use of a broadband single source emitting the wavelengths $\lambda_E$, $\lambda_{F1}$ and $\lambda_{F2}$, a narrowband spectral filter (typically <40 nm) can advantageously be placed in front of each of the detectors 62, 64 and 66 to allow only a narrow spectral band around $\lambda_E$, $\lambda_{F1}$ and $\lambda_{F2}$ respectively to pass.

An exemplary implementation of the method according to the present description, in which a second wavelength $\lambda_{F1}$ is used to characterize the single-mode optical fiber 30, is described first.

According to this example, the polarimetric characterization of the optical fiber at the second wavelength $\lambda_{F1}$ is carried out, then a Mueller matrix associated with the optical fiber at the second wavelength $\lambda_{F1}$ is determined. A Mueller matrix ($M_F$) associated with the optical fiber at the first wavelength $\lambda_E$ is deduced from the Mueller matrix associated with the optical fiber at the second wavelength $\lambda_{F1}$. Simultaneously with the characterization of the optical fiber at the second wavelength $\lambda_{F1}$, a polarimetric characterization of the assembly comprising the optical fiber and the sample is obtained at the first wavelength $\lambda_E$ by analysis of the polarization states of a wave retroreflected and/or backscattered by the sample. A Mueller matrix ($M_T$) associated with said assembly at the first wavelength $\lambda_E$ is obtained from this characterization. It is then possible, from the Mueller matrices associated respectively with the optical fiber ($M_F$) and with the assembly comprising the optical fiber and the sample ($M_T$), to determine the Mueller matrix ($M_O$) associated with the sample at the wavelength $\lambda_E$.

It should be noted that the polarimetric characterization of the optical fiber generally comprises the characterization of the optical fiber and of all the elements included between the output end of the optical fiber (distal end) and the reflector 40. In some cases, this characterization will be able to be compared to a characterization of the optical fiber alone, either because there are no other elements, or because these elements do not modify the polarization. Moreover, the optical elements which may be located between the selective reflector 40 and the sample S are chosen to be of a kind not to modify the polarization of the propagated waves. Such is the case for example of lenses, or other optical elements such as frequency-selective mirrors, or more generally plates consisting of optically isotropic materials and, if necessary, bearing dielectric or metallic layers, these plates being used at incidences very close to the normal (typical tolerance of the order of 5°).

The polarimetric characterization at a given wavelength of an object to be analyzed, in this case the optical fiber or the optical fiber/sample assembly, is done in a manner that is known and described for example in the European patent EP 1411333. The light wave is sent to the polarization state generator PSG, which can for example be electrically controlled, in order to define the four probe polarization states. Advantageously, these polarization states are as independent as possible. They are then distributed over the Poincaré sphere according to a regular tetrahedron. In practice, it is possible to work with a greater number of probe polarization states but it is demonstrated that four probe states are the minimum number of probe states for the polarimetric analysis. To generate the probe polarization states, the PSG comprises, for example and in a known manner, a set of elements including a linear polarizer, a first electrically controllable liquid crystal cell, a quarter-wave plate and a second electrically controllable liquid crystal cell. The four Stokes vectors corresponding to the four polarization states thus generated are arranged in four columns to form a 4×4 modulation matrix denoted W. After interaction with the sample, the polarization states returned are analyzed by means of the polarization state analyzer PSA, which comprises elements identical to those of the PSG but arranged in the reverse order relative to the direction of the light, such that, for example, the light passes first of all through the second liquid crystal cell, then the quarter-wave plate, then the first liquid crystal cell and the linear polarizer. The Stokes vectors corresponding to the four polarization states analyzed by the PSA are arranged in four rows to form a 4×4 analysis matrix denoted A. Thus, for each of the four polarization states deriving from the PSG, the light intensity at the output of the PSA, according to each of the polarization states analyzed, is measured by means of a detector. A matrix B of the sixteen light intensity levels measured is obtained, such that:

$$B = A \cdot M \cdot W \qquad (4)$$

Where M is the Mueller matrix of the sample.

The inversion of the known matrices A and W then makes it possible to determine the Mueller matrix according to the formula:

$$M = A^{-1} \cdot B \cdot W^{-1} \qquad (5)$$

Advantageously, a calibration can be applied to correct imperfections and errors of alignment of the elements forming the PSG and PSA. Indeed, the modulation and analysis matrices W and A may be different from the values theoretically calculated as a function of the elements forming the polarization state generator and analyzer. To perform this calibration, it is possible for example to successively place, in the place of the sample, 4 calibration samples which will make it possible to respectively obtain four intensity matrices. From calibration algorithms described in the literature (see the abovementioned patent EP 1411333 for example), it is then possible to obtain the real modulation and analysis matrices W and A.

In the example of polarimetric characterization of a sample cited above, the PSG and PSA comprise liquid crystals (nematic or ferroelectric). Many other systems can be used for the implementation of the method according to the present description. For example, the PSG can control the polarization by means of Pockels cells (see for example E. Compain et al. "Complete Mueller matrix measurement with a single high frequency modulation," Thin Solid Films 313-314, 47-52, 1998) or by means of a photoelastic modulator (see for example E. Compain et al., "Complete high-frequency measurement of Mueller matrices based on a new coupled-phase modulator," Rev. Sci. Instrum. 68, 2671-2680-1997). These systems make it possible to code the four states of the PSG simultaneously on four different frequencies. On the PSA side, it is possible to envisage the use of amplitude divider systems, like the "DOAP" described by E. Compain et al. (see for example the U.S. Pat. No. 6,177,995 B1) and which uses a separating prism and four detectors in parallel. This type of PSA can advantageously be coupled with a frequency coding PSG; the signal from each of the detectors can thus be demodulated over the four frequencies of the PSG, the set of demodulated signals thus supplying the sixteen measurements from which the Mueller matrix can be obtained. An example of this type of instrument is described in the U.S. Pat. No. 6,175,412 B1. Other PSG and PSA use fixed linear polarizers and rotating retarders (see for example the U.S. Pat. No. 7,298,480 B2).

The implementation of the characterization method using the device shown in FIG. 3 makes it possible to measure, firstly, a Mueller matrix $M_{m1}(\lambda_{F1})$ of the optical fiber at the second wavelength $\lambda_{F1}$, such that:

$$M_{m1}(\lambda_{F1}) = Re(-\theta_1) \cdot M_F^R(\lambda_{F1}) \cdot M_F(\lambda_{F1}) \cdot R(\theta_1) \qquad (3)$$

where $M_F(\lambda_{F1})$ and $M_F^R(\lambda_{F1})$ are, respectively, the Mueller matrices of the optical fiber, on the forward and on the backward paths, and where $R(\theta_1)$ and $Re(-\theta_1)$ are, respectively, rotation matrices of angles $\theta_1$ and $-\theta_1$, $\theta_1$ being the angle that is unknown in principle between the neutral axes of the fiber at the input thereof and the reference frame of the laboratory in which the Stokes vectors are defined. Assuming the fiber behaves like a pure phase retarder, the product $M_F{}^R(\lambda_{F1})$. $M_F(\lambda_{F1})$ corresponds to the matrix of a pure linear phase retarder representing this fiber over a round trip. The angles $\theta_1$ and $-\theta_1$ are therefore determined such that the product $R(-\theta_1)^{-1} \cdot M_{m1}(\lambda_{F1}) \cdot R(\theta_1)^1 = M_F{}^R(\lambda_{F1}) \cdot M_F(\lambda_{F1})$ corresponds to the matrix of such a pure linear phase retarder. Alternatively, these angles may be known from the angular position of the fiber, the neutral axes of which being previously identified. If the fiber does not exhibit any chiral effects (circular diattenuation and delay), which is the case for a standard single-mode fiber if care is taken for not twisting it, the matrices $M_F{}^R(\lambda_{F1})$ and $M_F(\lambda_{F1})$ are those of two identical linear retarders. From the product $M_F{}^R(\lambda_{F1}) \cdot M_F(\lambda_{F1})$ measured directly, each of the matrices $M_F(\lambda_{F1})$ and $M_R{}^F(\lambda_{F1})$ of the fiber, respectively on the forward and on the backward paths, at the first wavelength $\lambda_E$, can easily be deduced. Now, the Mueller matrix $M_T$ at the first wavelength $\lambda_E$ of the optical fiber and sample assembly, which is moreover directly measured, is given by the equation:

$$M_T(\lambda_E) = M_F{}^R(\lambda_E) \cdot M_O \cdot M_F(\lambda_E) \qquad (4)$$

Where $M_O$ is the Mueller matrix sought for the sample at the wavelength $\lambda_E$.

In some cases, it may also be useful to determine the angle $\theta_2$ defining the azimuth of one of the specific axes of the fiber at its output, i.e. at its distal end, relative to the reference frame of the laboratory, in order to correct the matrix $M_O$ previously obtained of any chiral effects. In the case of polarization-maintaining fibers for example, this azimuth is linked to the fiber and can be determined "mechanically".

It is thus possible to deduce, by inversion of the matrices, the Mueller matrix of the sample:

$$M_O = (M_F{}^R(\lambda_E))^{-1} \cdot M_T(\lambda_E) \cdot (M_F(\lambda_E))^{-1} \qquad (5)$$

The method described above will be able to work well if the wavelengths $\lambda_{F1}$ and $\lambda_E$ are distinct but sufficiently close, that is to say exhibiting a difference less than 100 nm, advantageously less than 50 nm, and if the fiber behaves well as a linear retarder with neutral axes of well-identified directions, such that the optical fiber induces a phase delay $\delta\varphi_{F1}$ along the neutral axes that is sufficiently low (between 0 and $2\pi$). In this case, it is possible to deduce, from the matrix of the optical fiber at the second wavelength $\lambda_{F1}$, the matrix of the optical fiber at the first wavelength $\lambda_E$ by deducing the phase delay $\delta\varphi_E$ at $\lambda_E$ from the phase delay $\delta\varphi_{F1}$ at $\lambda_{F1}$ ($\delta\varphi_E = \delta\varphi_{F1} * \lambda_{F1}/\lambda_E$).

According to a second variant of the polarimetric characterization method that can be implemented also with a device such as that represented in FIG. 3, two wavelengths $\lambda_{F1}$, $\lambda_{F2}$ that are distinct from one another and distinct from the first wavelength $\lambda_E$ are used for the polarimetric characterization of the optical fiber.

Thus, according to this variant, the source of emission also allows the emission of a wave at a third wavelength $\lambda_{F2}$ distinct from the first and second wavelengths $\lambda_E$ and $\lambda_{F1}$. The selective reflector 40, for example a high-pass spectral filter, is adapted to allow the reflection of waves being propagated in the optical fiber at the second and third wavelengths $\lambda_{F1}$, $\lambda_{F2}$ and allows the wavelengths being propagated at the first wavelength $\lambda_E$ to pass if $\lambda_{F1} < \lambda_E < \lambda_{F2}$ is chosen.

According to this variant, a polarimetric characterization of the optical fiber at the second and third wavelengths $\lambda_{F1}$ and $\lambda_{F2}$ is performed, for example according to the means described previously, in order to determine a Mueller matrix associated with the optical fiber at the second wavelength ($\lambda_{F1}$) and a Mueller matrix associated with the optical fiber at the third wavelength ($\lambda_{F2}$). The measurement of the Mueller matrix at the wavelength $\lambda_{F1}$ makes it possible to determine a phase delay $\delta\varphi_{F1\_mes}$ equal to the real phase delay $\delta\varphi_{F1}$, modulo $2\pi$. In other words, the phase delay sought at $\lambda_{F1}$ is $\delta\varphi_{F1} = \delta\varphi_{F1\_mes} + 2m\pi$, with m being an integer. Similarly, the measurement of the Mueller matrix at the wavelength $\lambda_{F2}$ makes it possible to determine a phase delay $\delta\varphi_{F2\_mes}$ equal to the real phase delay $\delta\varphi_{F2}$, modulo $2\pi$. The phase delay sought at $\lambda_{F2}$ is $\delta\varphi_{F2} = \delta\varphi_{F2\_mes} + 2m'\pi$, with m' being an integer. Since the two wavelengths $\lambda_{F1}$ and $\lambda_{F2}$ are close, the ratio $\delta\varphi_{F1}/\delta\varphi_{F2}$ is, to the first order, equal to the inverse ratio of the wavelengths $\lambda_{F2}/\lambda_{F1}$. By ensuring that the residual phase shifts $\delta\varphi_{F1}$ and $\delta\varphi_{F2}$ remain small, which means that the integers m and m' remain small, typically less than 5, the pair (m,m') making it possible to observe the condition $\delta\varphi_{F1}/\delta\varphi_{F2} = \lambda_{F2}/\lambda_{F1}$ can be easily identified, which makes it possible to deduce the values of $\delta\varphi_{F1}$ and $\delta\varphi_{F2}$. In a second stage, the phase delay $\delta\varphi_E$ at $\lambda_E$ is calculated by the rule of three: $\delta\varphi_E = \delta\varphi_{Fi} * \lambda_{Fi}/\lambda_E$ (i=1 or 2). It is thus possible to deduce the matrices of the optical fiber on the forward path and on the backward path at the wavelength $\lambda_E$ and to determine the matrix sought for the sample, as explained previously (equation 5).

In practice, the current technology of standard single-mode fibers presents the drawback of exhibiting an orientation of the neutral axes that is not sufficiently well defined and that can vary according to stresses, temperature, etc. It may be preferable according to a variant to use polarization-maintaining fibers for which the orientation of the neutral axes at the input and at the output is known and fixed. However, it turns out that the phase delay introduced by a standard polarization-maintaining optical fiber is significant (typically $\pi$ per mm), which can be problematic for the implementation of the method according to the variants described by means of FIG. 3.

The applicants have developed a single-mode optical fiber that is particularly advantageous for the implementation of the polarimetric characterization method according to the present description.

This optical fiber, hereinafter in the description called "polarization-maintaining and compensated delay single-mode fiber", comprises two sections of a same polarization-maintaining single-mode fiber, of equal lengths, connected together (by a weld for example), the fast axis of the first section being aligned with the slow axis of the second section. With this arrangement, the direction of the neutral axes of this fiber, at the input as at the output, can be easily determined by placing it between cross polarizers and by seeking the extinction of the transmitted field. In this situation in effect, the direction of the input (respectively output) polarizer is that of one of the neutral axes of the fiber at the input (respectively at the output). Thus, if the lengths of the sections are strictly equal and if the two sections are conditioned in the same way (same bends, same temperature, etc.), it is expected that the phase delay added by the polarization-maintaining and compensated delay single-mode fiber between the two components of the injected field is zero or negligible, the second section exactly compensating the first one. In reality, a slight difference in length between the two fibers and/or the conditioning and/or an environment that are different for the two sections can induce the existence of a residual phase shift, added by the polarization-maintaining and compensated delay single-mode fiber between the two components of the field at the output of the fiber. The applicants have shown that this residual phase shift could be less than $8\pi$ regardless of the length of the fiber, even below $4\pi$. The method as described previously will then make it possible, by measurement of the Mueller matrix of the optical fiber at a second wavelength $\lambda_{F1}$, even at two wavelengths $\lambda_{F1}$, $\lambda_{F2}$ as has been described, to perfectly determine the matrix of the optical fiber at the first wavelength $\lambda_E$ and to deduce therefrom the Mueller matrix of the sample. Moreover, such a fiber exhibits little chiral effects.

Figure 4:
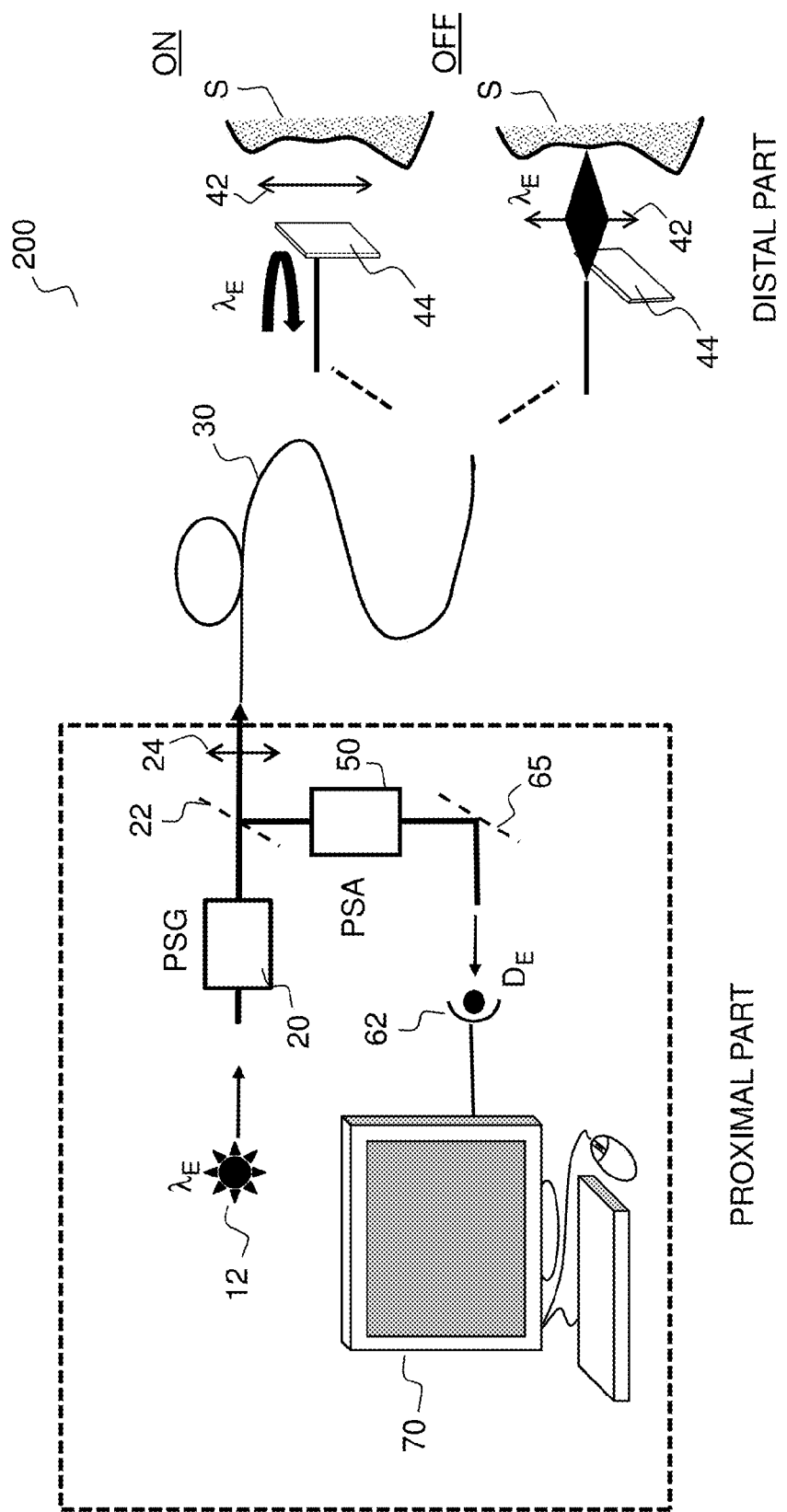
FIG. 4, a diagram illustrating a polarimetric characterization device according to the present description, according to a second example.

FIG. 4 represents a polarimetric characterization device 200 according to a second example, for the implementation of a polarimetric characterization method according to the present description.

The device 200 comprises a number of elements identical to the elements of the device 100 and which are not described again, notably including the PSG 20 and PSA 50, the single-mode optical fiber 30, the processing means 70.

According to this variant, the source of emission comprises only one source of emission 12 emitting at the first wavelength $\lambda_E$, for example a laser diode, and a detector at the output of the PSA sensitive to this same wavelength, for example a photodiode.

The selective reflector described in FIG. 3 is replaced by a removable reflector, for example a switchable reflector, for example of MEMS type, that can operate in an ON mode when it is positioned at the fiber output and OFF mode when it is separated from the end of the fiber, as is illustrated in FIG. 4.

According to this variant, it is possible to alternately perform a characterization of the optical fiber directly at the wavelength of interest $\lambda_E$, then a characterization of the assembly comprising the optical fiber and the sample also at this same wavelength. If the characterizations of the fiber and of the fiber/sample assembly are done in a sufficiently short time (typically less than 10 ms), it is possible to implement the method with a simple single-mode optical fiber or a standard polarization-maintaining single-mode optical fiber. Obviously, this method can also be implemented with the polarization-maintaining and compensated delay single-mode optical fiber as described previously.

The Mueller matrix of the sample can then be determined from the Mueller matrices of the fiber and of the assembly comprising the fiber and the sample, as explained previously (equation 5).

Figure 5:
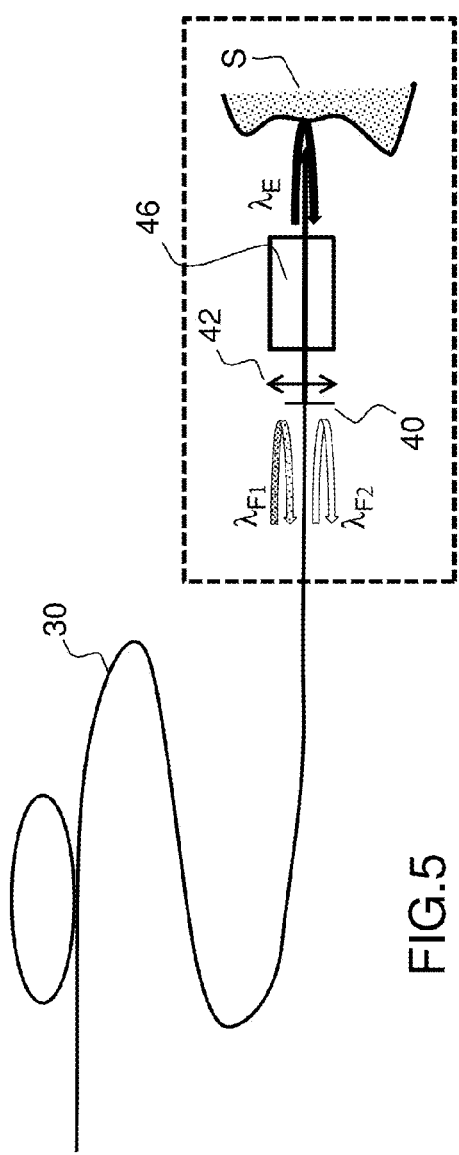
FIG. 5, a diagram showing, according to a partial view, a variant of a polarimetric characterization device according to the present description.

FIG. 5 shows a variant applicable to one or other of the examples of devices described by means of FIGS. 3 and 4.

According to this variant, a scanning system 46 is arranged on the proximal side, after the focusing means 42. In another arrangement, the scanning system 46 can be placed between the fiber 30 and the focusing means 42. In this case, it can advantageously be preceded by means for collimating the beam outgoing from the fiber 30. The scanning system makes it possible to scan the sample in order to reconstruct an image of a region of interest.

The applicants have also shown that it was possible, by virtue of a micro-scanning over a set of neighboring points of the sample, to dispense with artifacts which could result from a spot measurement. In particular, the Mueller matrix measured at the point of focusing of the beam on an object can reveal a depolarization rate lower than the depolarization rate which would be obtained by analyzing a wider region. The depolarization rate produced by such a wider region can be obtained from the average of a series of Mueller matrices measured on an ad hoc basis at various points of this region.

FIGS. 7 to 11 show first experimental results obtained with the method according to the present description.

Figure 6:
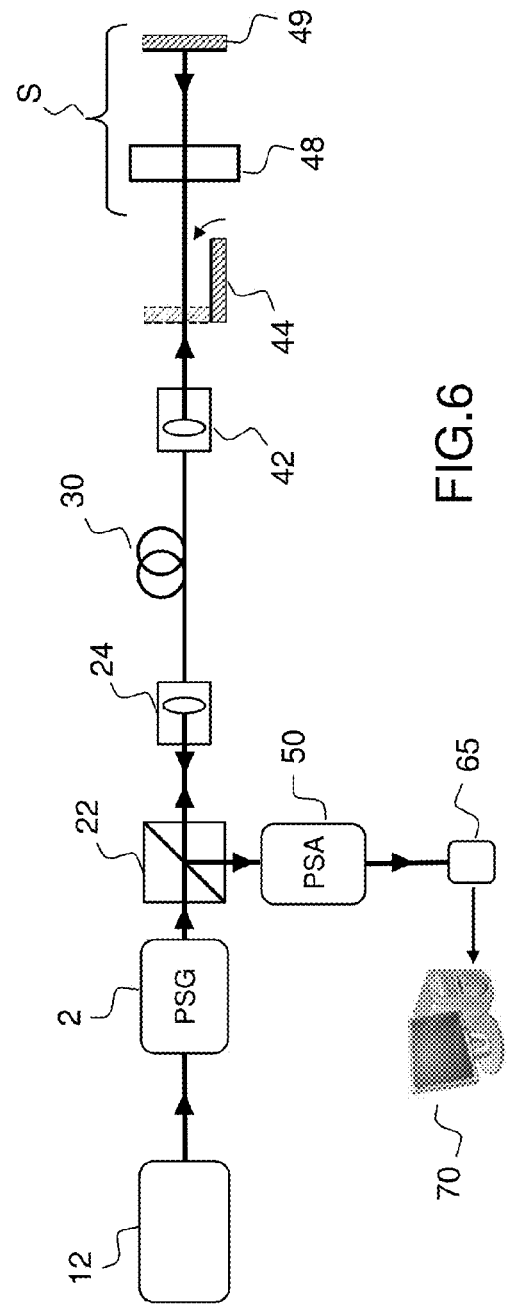
FIG. 6, a diagram illustrating an experimental setup used for the experimental validation of an exemplary characterization method according to the present description.

These first results are obtained with a device of the type of that of FIG. 4 and on well calibrated "test" samples. FIG. 6 shows the experimental setup implemented for these validations. All of the elements used are identical to those represented in FIG. 4 but the sample S is formed here by a calibrated object of analysis 48 and a plane mirror 49.

Figure 7:
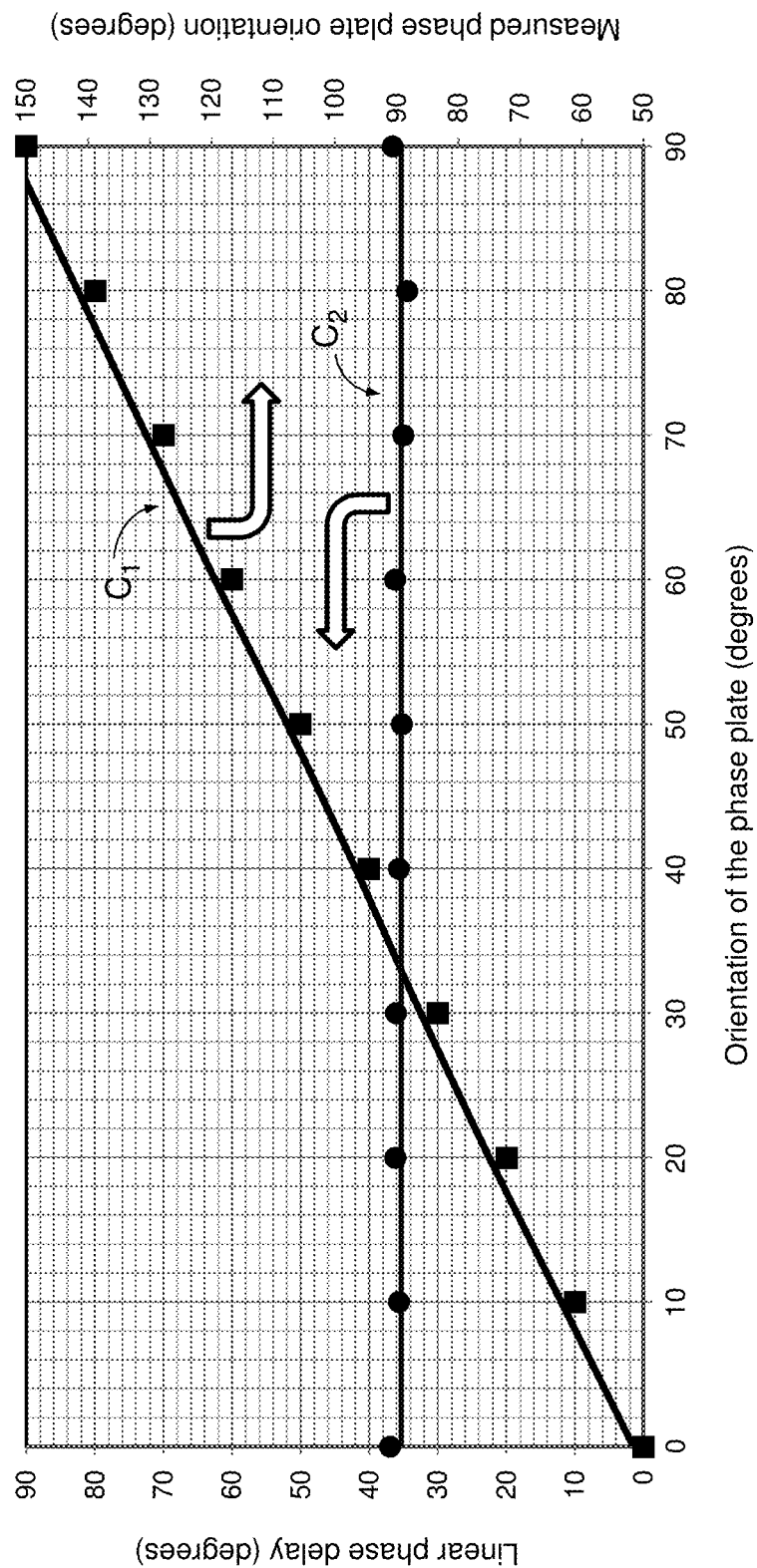
FIGS. 7 and 8, experimental curves obtained with the diagram shown in FIG. 6 and compared with expected theoretical values.

In the case of the results shown in FIG. 7, the sample is formed by a wave plate of $\lambda/8$ plate type followed by a mirror. The $\lambda/8$ plate introduces a phase delay of 45° between its neutral axes when it is passed through in a single passage by the light. This plate is turned into the plane at right angles to the direction of propagation of the light so as to vary the orientation of its neutral axes relative to the reference frame of the laboratory. The curve C1 shows the orientation given to the plate relative to an arbitrary reference orientation, lying between 0° and 90° (solid lines), and the orientation measured by the device (dots). The curve C2 shows, for each of these orientations, the phase delay measured for this plate. This delay, equal to 90°, corresponds to the aggregate phase delay on the dual passage through the $\lambda/8$ plate (forward and backward) analyzed.

Figure 8:
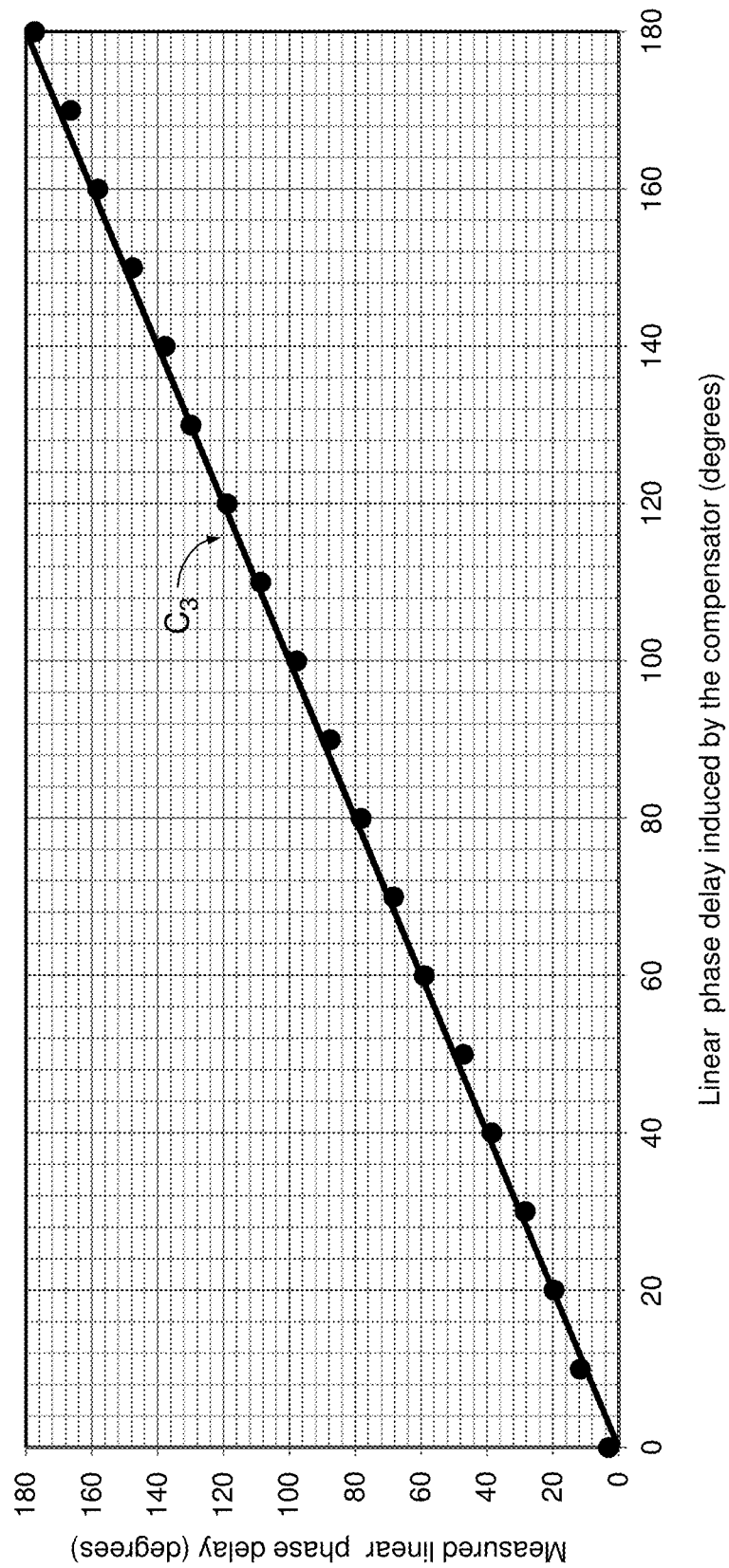

In the case of the results shown in FIG. 8, the sample consists of a Babinet-Soleil compensator followed by a mirror. The Babinet-Soleil compensator introduces a known and adjustable phase delay between its neutral axes when it is passed through by the light. The curve C3 shows the linear phase delay introduced on a round trip of the light adjusted by setting the Babinet-Soleil compensator (solid lines) and the corresponding measured phase delay (dots).

Figure 9A:
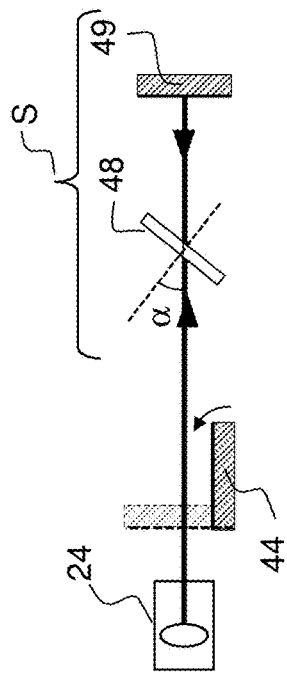
FIG. 9A, a partial diagram of the diagram of FIG. 6, showing a sample used for the validation of an exemplary characterization method according to the present description.
Figure 9B:
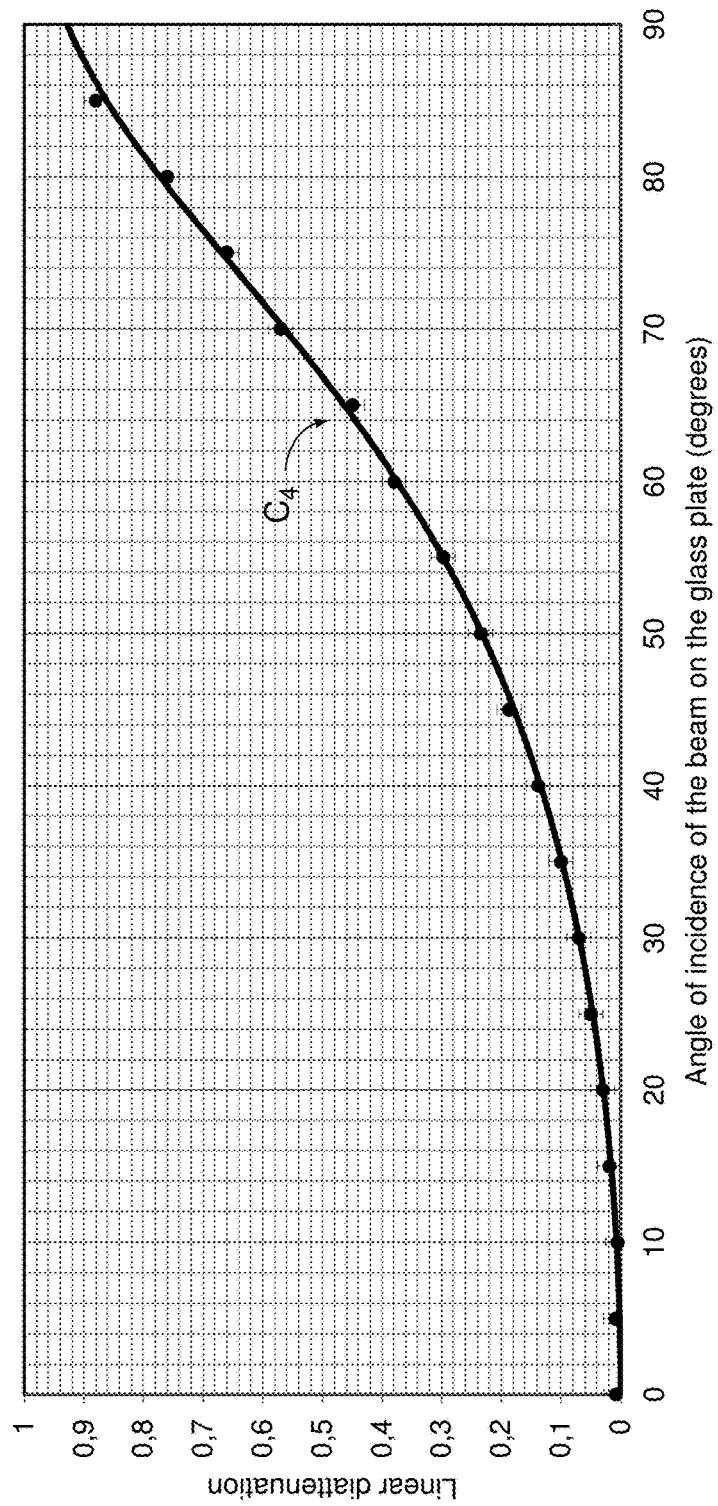
FIG. 9B, experimental curves obtained with the sample shown in FIG. 9A and compared with expected theoretical values.

FIG. 9A illustrates a sample consisting of a plate with parallel faces 48 followed by a mirror 49. The faces of the plate are at right angles to the plane of incidence of the light beam from the collimation system 24 and their normal direction is inclined by an angle α that can be adjusted relative to the direction of the beam. This plate therefore behaves as a pure linear diattenuator component whose diattenuation can be adjusted via the angle α. FIG. 9B shows the linear diattenuation of the plate with parallel faces on a round trip of the light (solid lines) calculated as a function of the angle α and the corresponding measured linear diattenuation (dots). It is also shown that, for each of these dots, the circular diattenuation and the linear phase delay measured are zero.

Figure 10A:
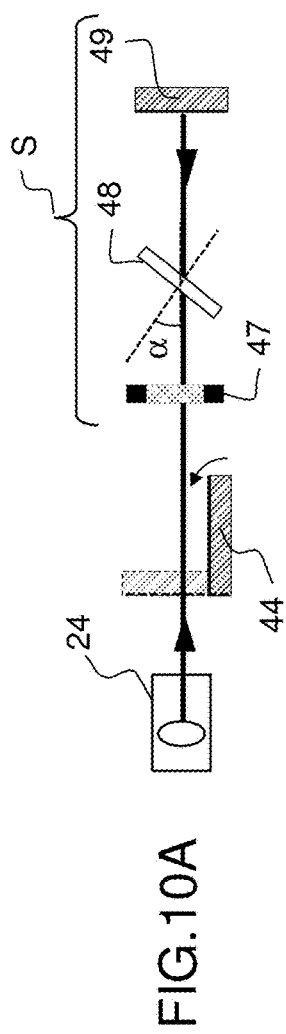
FIG. 10A, a partial diagram of the diagram of FIG. 6, showing a sample used for the validation of an exemplary characterization method according to the present description.

FIG. 10A shows a sample consisting of a Babinet-Soleil compensator 47, followed by a plate with parallel faces 48 and a mirror 49. The plate with parallel faces is positioned relative to the incident beam as in the case of FIG. 9A. In this arrangement, the normal to the plate is inclined relative to the incident beam by an angle α such that it introduces a linear diattenuation of 35% on a round trip of the light. With regard to the Babinet-Soleil compensator, its fast axis is oriented, in the plane at right angles to the beam, so that it forms an angle of 45° relative to the axis of rotation of the plate. With this arrangement, with the plate remaining fixed, the phase delay introduced by the Babinet compensator is adjusted between 0° and 90° for a single passage, that is to say between 0° and 180° for a round trip of the light.

Figure 10B:
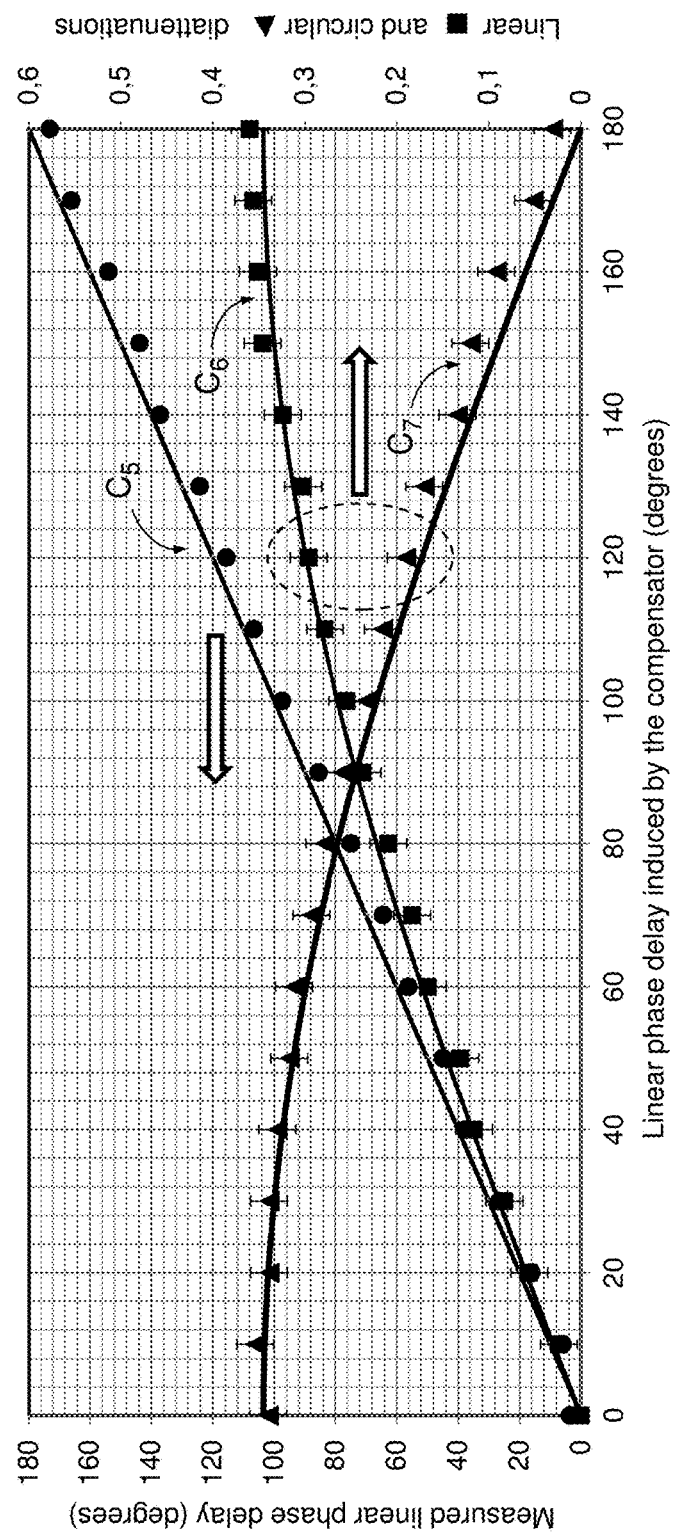
FIG. 10B, experimental curves obtained with a sample of the type of that shown in FIG. 10A and compared with expected theoretical values.

The numerical simulations show that, when the Babinet-Soleil compensator is set to introduce a phase delay γ of between 0° and 90° upon a single passage, the compensator+plate with parallel faces assembly behaves as a component introducing a phase delay 2γ on a round trip and a combination of linear $D_L$ and circular $D_C$ diattenuations such that the resulting diattenuation $D=\sqrt{D_L^2+D_c^2}=35\%$. When γ=0°, the diattenuation is a pure linear diattenuation $D=D_L=35\%$ and when γ=90°, the diattenuation is a pure circular diattenuation $D=D_c=35\%$. The curves C5, C6 and C7 of FIG. 10B show, by solid lines, the results of the simulations respectively calculating the phase delay, the circular diattenuation and the linear diattenuation in the arrangement of FIG. 10A. The points associated with the curves C5, C6 and C7 show the results of the corresponding experimental measurements.

Figure 11A:
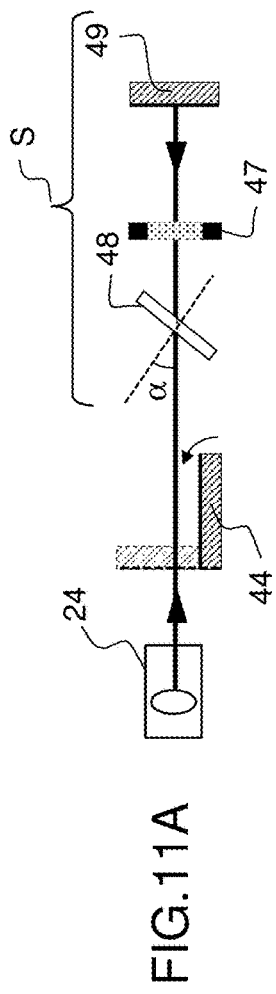
FIG. 11A, a partial diagram of the diagram of FIG. 6, showing another sample used for the validation of an exemplary characterization method according to the present description.

FIG. 11A shows a sample identical to that of FIG. 10A but in which the order of the components is reversed. In other words, the sample consists of a plate with parallel faces 48 followed by a Babinet-Soleil compensator 47 and a mirror 49, all the other settings being kept identical to those of FIG. 10A.

Figure 11B:
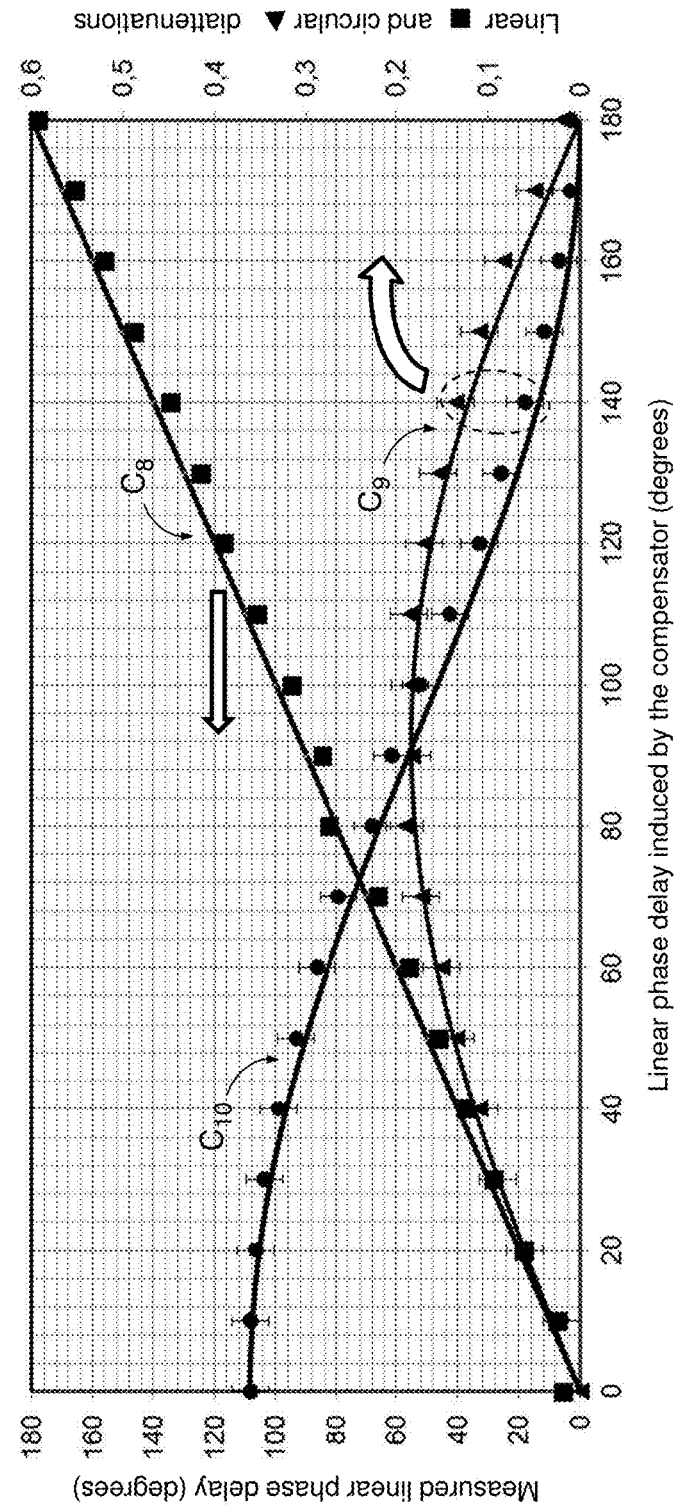
FIG. 11B, experimental curves obtained with a sample of the type of that shown in FIG. 11A and compared with expected theoretical values.

The numerical simulations show that, when the Babinet-Soleil compensator is set to introduce a phase delay γ of between 0° and 90° upon a single passage, the compensator+plate with parallel faces assembly behaves as a component introducing a phase delay 2γ on a round trip and a combination of linear $D_L$ and circular $D_C$ diattenuations such that the linear diattenuation decreases from 35% to 0% when the phase delay γ changes from 0° to 90°, and the circular diattenuation increases from 0% to 17.5% then decreases to 0% when the phase delay γ changes from 0° to 90°. The curves C8, C9 and C10 of FIG. 11B show, by solid lines, the results of the simulations respectively calculating the phase delay, the circular diattenuation and the linear diattenuation in the arrangement of FIG. 11A. The points associated with the curves C8, C9 and C10 show the results of the corresponding experimental measurements.

The experimental results thus presented show the feasibility of the polarimetric characterization method according to the present description and the possibilities of accessing polarimetric information concerning the sample that is comprehensive and accurate, notably the linear phase delays and the linear and circular diattenuations.

The method thus described will be able to be implemented not only for the polarimetric characterization of biological samples in endoscopy but also for the characterization of samples that are difficult to access, such as, for example, the characterization of insulating or conductive materials in a hostile environment (presence of nuclear radiations, strong electromagnetic fields, very high or very low temperatures, etc.).

Although described through a number of detailed exemplary embodiments, the polarimetric characterization method and device according to the invention comprise different variants, modifications and refinements which will be obvious to those skilled in the art, on the understanding that these different variants, modifications and refinements form part of the scope of the invention, as defined by the following claims.

The invention claimed is:

1. A device for remote polarimetric characterization of a sample comprising:
   a source of emission of at least one incident light wave that has at least one first wavelength;
   a single-mode optical fiber in which the incident light wave is propagated;
   a polarization state generator (PSG) arranged on the proximal side of the optical fiber and making it possible to generate a given number of polarization states of the incident light wave, called probe states;
   a reflector intended to be arranged on the distal side of the optical fiber;
   a polarization state analyzer (PSA) arranged on the proximal side of the optical fiber and allowing, for each probe state of the incident wave, the analysis of the polarization of the light wave obtained after propagation of the incident wave in the optical fiber, reflection on the distal side of the optical fiber and back propagation in the optical fiber;
   a processor for determining:
      a Mueller matrix associated with the optical fiber at the first wavelength from a first polarimetric characterization of the optical fiber, obtained by analysis for each probe state, of the polarization of at least one wave reflected on the distal side of the optical fiber by means of the reflector and propagated in the back direction in the optical fiber;
      a Mueller matrix associated with an assembly comprising the optical fiber and the sample at the first wavelength from a second polarimetric characterization of said assembly, obtained by analysis for each probe state of the polarization, of a wave returned from the distal side of the fiber by the sample and propagated in the back direction in the optical fiber; and
      a Mueller matrix associated with the sample at the first wavelength from the Mueller matrices associated respectively with the optical fiber and with the assembly comprising the optical fiber and the sample.

2. The polarimetric characterization device as claimed in claim 1, wherein:
   the source of emission allows the emission of a wave at the first wavelength and the emission of a wave at a second wavelength distinct from the first wavelength,
   the reflector is a spectral reflector allowing the reflection of a wave being propagated in the optical fiber at the second wavelength for the polarimetric characterization of the optical fiber at the second wavelength and the passage of the wave at the first wavelength for the polarimetric characterization of the assembly comprising the optical fiber and the sample at the first wavelength;
   the processor further determining:
      from the polarimetric characterization of the optical fiber at the second wavelength, a Mueller matrix associated with the optical fiber at the second wavelength;
      from the Mueller matrix associated with the optical fiber at the second wavelength, the Mueller matrix associated with the optical fiber at the first wavelength.

3. The polarimetric characterization device as claimed in claim 2, wherein:
   the source of emission also allows the emission of a wave at a third wavelength distinct from the first and second wavelengths,
   the spectral reflector allows the reflection of waves being propagated in the optical fiber at the second and third wavelengths for the polarimetric characterization of the optical fiber at the second and third wavelengths;
   the processor for determining:
      from a polarimetric characterization of the optical fiber at the second wavelength and from a polarimetric characterization of the optical fiber at the third wavelength, respectively the Mueller matrix associated with the optical fiber at the second wavelength and a Mueller matrix associated with the optical fiber at the third wavelength;
      from the Mueller matrices associated with the optical fiber at the second wavelength and third wavelength, the Mueller matrix associated with the optical fiber at the first wavelength.

4. The polarimetric characterization device as claimed in claim 1, wherein the reflector is a reflector that can be switched between a reflecting position and a passing position, allowing, in the reflecting position, the reflection of a wave being propagated in the optical fiber at the first wavelength for the polarimetric characterization of the optical fiber and, in the passing position, the reflection of the wave by the sample for the polarimetric characterization of the assembly comprising the optical fiber and the sample.

5. The device as claimed in claim 1, wherein the single-mode optical fiber is a polarization-maintaining optical fiber.

6. The device as claimed in claim 5, wherein the single-mode optical fiber comprises a first section of a polarization-maintaining single-mode optical fiber and a second section of the same polarization-maintaining single-mode optical fiber, the sections being of the same length and connected together such that the fast axis of the first section is aligned with the slow axis of the second section and vice versa.

7. The device as claimed in claim 1, further comprising, on the distal side of the optical fiber, an optical element for focusing a wave at the first wavelength for the characterization of a spot zone of the sample.

8. The device as claimed in claim 7, further comprising, on the distal side of the optical fiber, a scanning system for the polarimetric characterization of a set of spot zones of the sample.

9. A method for remote polarimetric characterization of a sample comprising:
   the emission of an incident light wave that has at least one first wavelength that is propagated in a single-mode optical fiber;
   the polarimetric characterization of the optical fiber at the first wavelength, comprising:
   the generation of a given number of polarization states of the incident light wave, called probe states, by a polarization state generator (PSG) arranged on the proximal side of the optical fiber;
   the analysis, by a polarization state analyzer (PSA) arranged on the proximal side of the optical fiber, for each probe state of the incident wave, of the polarization of the light wave obtained after propagation of the incident wave in the optical fiber, reflection by a reflector (40, 44) arranged on the distal side of the optical fiber and back propagation in the optical fiber;
   the determination of a Mueller matrix associated with the optical fiber at the first wavelength;
   the polarimetric characterization of an assembly comprising the optical fiber and the sample at the first wavelength, comprising:
      by said polarization state generator (PSG) and polarization state analyzer (PSA), the analysis, for each probe state of the polarization, of a wave returned from the distal side of the fiber by the sample and propagated in the reverse direction in the optical fiber;
      the determination of a Mueller matrix associated with said assembly at the first wavelength;
   the determination of a Mueller matrix associated with the sample at the first wavelength from the Mueller matrices associated respectively with the optical fiber and with the assembly comprising the optical fiber and the sample.

10. The polarimetric characterization method as claimed in claim 9, comprising:
   the emission of a light wave at a second wavelength distinct from the first wavelength,
   and wherein:
   the reflector is a spectral reflector allowing the reflection of a wave being propagated in the optical fiber at the second wavelength for the polarimetric characterization of the optical fiber at the second wavelength and the passage of the wave at the first wavelength for the polarimetric characterization of the assembly comprising the optical fiber and the sample at the first wavelength;
   the determination of the Mueller matrix associated with the optical fiber at the first wavelength comprises:
   from the polarimetric characterization of the optical fiber at the second wavelength, a Mueller matrix associated with the optical fiber at the second wavelength;
   from the Mueller matrix associated with the optical fiber at the second wavelength, the Mueller matrix associated with the optical fiber at the first wavelength.

11. The polarimetric characterization method as claimed in claim 10, comprising:
   the emission of a wave at a third wavelength distinct from the first and second wavelengths,
   and wherein:
   the spectral reflector allows the reflection of waves being propagated in the optical fiber at the second and third wavelengths for the polarimetric characterization of the optical fiber at the second and third wavelengths;
   the determination of the Mueller matrix associated with the optical fiber at the first wavelength comprises:
   from a polarimetric characterization of the optical fiber at the second wavelength and from a polarimetric characterization of the optical fiber at the third wavelength, respectively the Mueller matrix associated with the optical fiber at the second wavelength and a Mueller matrix associated with the optical fiber at the third wavelength;
   from the Mueller matrices associated with the optical fiber at the second wavelength and third wavelength, the Mueller matrix associated with the optical fiber at the first wavelength.

12. The polarimetric characterization method as claimed in claim 9, wherein the reflector is a reflector that can be switched between a reflecting position and a passing position, allowing, in the reflecting position, the reflection of a wave being propagated in the optical fiber at the first wavelength for the polarimetric characterization of the optical fiber and, in the passing position, the reflection of the wave by the sample for the polarimetric characterization of the assembly comprising the optical fiber and the sample.

13. The method as claimed in claim 9, further comprising, on the distal side of the optical fiber, the focusing of a light wave at the first wavelength by an optical element for the characterization of a spot zone of the sample.

14. The method as claimed in claim 13, further comprising, on the distal side of the optical fiber, the scanning by a scanning system of the focused light wave for the polarimetric characterization of a set of spot zones of the sample.

* * * * *